United States Patent
Kawana et al.

(10) Patent No.: US 7,858,933 B2
(45) Date of Patent: Dec. 28, 2010

(54) MASS SPECTROMETER

(75) Inventors: Shuichi Kawana, Osaka (JP); Manabu Shimomura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 215 days.

(21) Appl. No.: 12/281,706

(22) PCT Filed: Mar. 7, 2006

(86) PCT No.: PCT/JP2006/304372

§ 371 (c)(1),
(2), (4) Date: Sep. 4, 2008

(87) PCT Pub. No.: WO2007/102202

PCT Pub. Date: Sep. 13, 2007

(65) Prior Publication Data

US 2009/0039252 A1  Feb. 12, 2009

(51) Int. Cl.
 *B01D 59/44* (2006.01)
(52) U.S. Cl. .............. 250/288; 250/427; 250/423 R
(58) Field of Classification Search .......... 250/288, 250/432 R, 427, 423 F
See application file for complete search history.

(56) References Cited

U.S. PATENT DOCUMENTS

| | | | |
|---|---|---|---|
| 3,555,272 A * | 1/1971 | Munson | 250/424 |
| 3,602,752 A * | 8/1971 | Shriner | 250/298 |
| 7,291,845 B2 * | 11/2007 | Moeller et al. | 250/427 |

FOREIGN PATENT DOCUMENTS

| | | |
|---|---|---|
| JP | 09-190799 A | 7/1997 |
| JP | 10-302660 A | 11/1998 |
| JP | 2002-373616 A | 12/2002 |
| JP | 2003-257360 A | 9/2003 |
| JP | 2005-259482 A | 9/2005 |

\* cited by examiner

*Primary Examiner*—Kiet T Nguyen
(74) *Attorney, Agent, or Firm*—Sughrue Mion, PLLC

(57) ABSTRACT

A filament 3 for generating thermions is remotely located from an ionization chamber 2 so that a thermion-accelerating electric field created by a potential difference between the filament 3 and the ionization chamber 2 is prevented from penetrating through an electron injection port 5 into the ionization chamber 2. This design eliminates the disturbance of an ion-extracting electric field created within the ionization chamber 2 by a voltage applied to lens electrodes 13, thus enabling ions produced within the ionization chamber 2 to be efficiently extracted and transported to a mass analyzer located at the subsequent stage. As a result, the level of detection signals of a detector is increased, so that the mass analysis can be performed with high sensitivity.

4 Claims, 1 Drawing Sheet

MASS SPECTROMETER

TECHNICAL FIELD

The present invention relates to a mass spectrometer having an ion source that performs electron ionization, and specifically to the structure of the ion source.

BACKGROUND ART

A mass spectrometer is a device that ionizes molecules or atoms of a sample, then separates the resultant ions according to their mass-to-charge ratio and detects these ions. Various methods for ionizing sample molecules have been developed to date, and electron ionization (EI) is one of the most generally used methods. In electron ionization, sample molecules are introduced into an ionization chamber of a comparatively small capacity, which is placed under a vacuum atmosphere. A filament for generating thermions is provided outside this ionization chamber, and thermions thereby generated are accelerated and injected into the ionization chamber. These thermions come in contact with the sample molecules to ionize these molecules within the ionization chamber. The ions thus produced within the ionization chamber are extracted to the outside by the action of an electric field created by a voltage applied to ion-extracting electrodes (e.g. a lens optical system) provided outside the ionization chamber.

To accelerate the thermions generated by the filament, an electric field with a potential gradient is created between the filament and the ionization chamber by providing a potential difference between them. Due to the action of this electric field, the thermions move toward the ionization chamber and enter the same chamber through an electron injection port provided in the wall of the ionization chamber. In normal modes of electron ionization, the thermions should gain an acceleration energy of approximately 70 eV. Accordingly, the potential difference between the filament and the ionization chamber is set at approximately 70 V.

In an ion source that performs electron ionization, the thermions generated by the filament should be efficiently introduced into the ionization chamber to improve the ionization efficiency within this chamber. For this purpose, the filament in the conventional ion sources is located relatively close to the electron injection port bored in the wall of the ionization chamber. However, if the filament is placed in the vicinity of the electron injection port, the electric field created by the potential difference between the filament and the ionization chamber may penetrate into the ionization chamber and disturb an ion-extracting electric field within the ionization chamber, which is mainly created by the potential difference between the lens optical system and the ionization chamber. Such a disturbance of the electric field will impede the extraction of ions from the ionization chamber.

Patent Document 1: Japanese Unexamined Patent Application Publication No. 2002-373616

DISCLOSURE OF THE INVENTION

Problem to be Solved by the Invention

In summary, in the conventional ion source, the ion extraction efficiency is sacrificed as a result of attaching too much importance to the ion production efficiency, so that the overall ion detection sensitivity is decreased. The present invention has been developed to solve this problem, and its objective is to provide a mass spectrometer whose detection sensitivity can be improved by efficiently extracting ions produced in the ionization chamber to the outside of the same chamber and using these ions for mass analysis.

Means for Solving the Problems

To solve the previously described problem, the present invention provides a mass spectrometer having an ion source that performs electron ionization, the ion source having a filament for generating thermions by heating and an ionization chamber in which sample molecules are ionized by the thermions, the ionization chamber having an electron injection port through which the thermions are introduced into the inner space thereof, wherein:

the filament is located at a place so remote from the ionization chamber that the inner space of the ionization chamber is free from the influence of an electric field created in the space between the filament and the electron injection port by a potential difference between the filament and the ionization chamber.

Increasing the distance between the filament and the ionization chamber makes it more difficult for the thermions generated by the filament to pass through the electron injection port and enter the ionization chamber. Therefore, the ion production efficiency will deteriorate if the other conditions are identical. On the other hand, increasing the distance between the filament and the ionization chamber also makes it more difficult for the electric field created by the potential difference between the filament and the ionization chamber to penetrate into the ionization chamber. Therefore, the ion extraction efficiency (i.e. the efficiency of extracting ions from the ionization chamber through the normal ion ejection port and using them for mass analysis) will improve. In conventional mass spectrometers, the former efficiency was taken into primary consideration, so that the latter efficiency was low and the overall ion detection sensitivity was not optimized. On the other hand, in the mass spectrometer according to the present invention, the filament is distanced from the ionization chamber (i.e. the electron injection port) to balance the two aforementioned efficiencies so that the ion detection sensitivity will be higher than in the conventional cases.

In a preferable mode of the present invention, the ratio Db/Da is 1.7 or larger, where Da is the distance between the inner surface of the wall of the ionization chamber in which the electron injection port is formed and the center of the ionization chamber, and Db is the distance between the filament and the center of the ionization chamber. Although, this ratio was conventionally set at 1.5 or smaller, it has been found that setting Db/Da at 1.7 or larger increases the signal strength by approximately 40% if the other conditions are identical. The upper limit of Db/Da should be preferably set at 3.0 or smaller, although the preferable upper limit depends on the potential difference between the ionization chamber and the filament, and also on the position and magnetic force of a magnet, which is generally located outside the filament, for generating a thermion-converging magnetic field.

Increasing the opening area of the electron injection port strengthens the influence of the thermion-accelerating electric field within the ionization chamber. Accordingly, in a preferable mode of the present invention, the ratio A/(Db-Da) is within a range from 0.45 to 4.037 under the condition that the potential difference between the filament and the ionization chamber is within a range from 10 to 200[V], where A is the opening area (in units of $mm^2$) of the electron injection port and Db-Da is the distance (in units of mm) between the filament and the inner surface of the wall of the ionization chamber in which the electron injection port is formed. In normal ion sources for electron ionization, the values of the opening area of the electron injection port of the ionization chamber fall within a certain range. Selecting the value of A/(Db-Da) within the aforementioned range will more assuredly prevent the thermion-accelerating electric field from having unfavorable influences within the ionization chamber.

Effect of the Invention

Thus, in the mass spectrometer according to the present invention, the thermion-accelerating electric field created by the potential difference between the filament and the ionization chamber is prevented from penetrating through the electron injection port into the ionization chamber. Accordingly, there is no disturbance of the ion-extracting electric field created within the ionization chamber by the lens optical system, and ions generated within the ionization chamber can be efficiently extracted through the ion ejection port and transported to the mass analyzer section by the lens optical system. Thus, the detection sensitivity is improved as compared to the conventional levels, so that the mass analysis can be performed with high sensitivity.

BEST MODE FOR CARRYING OUT THE INVENTION

Figure 1:
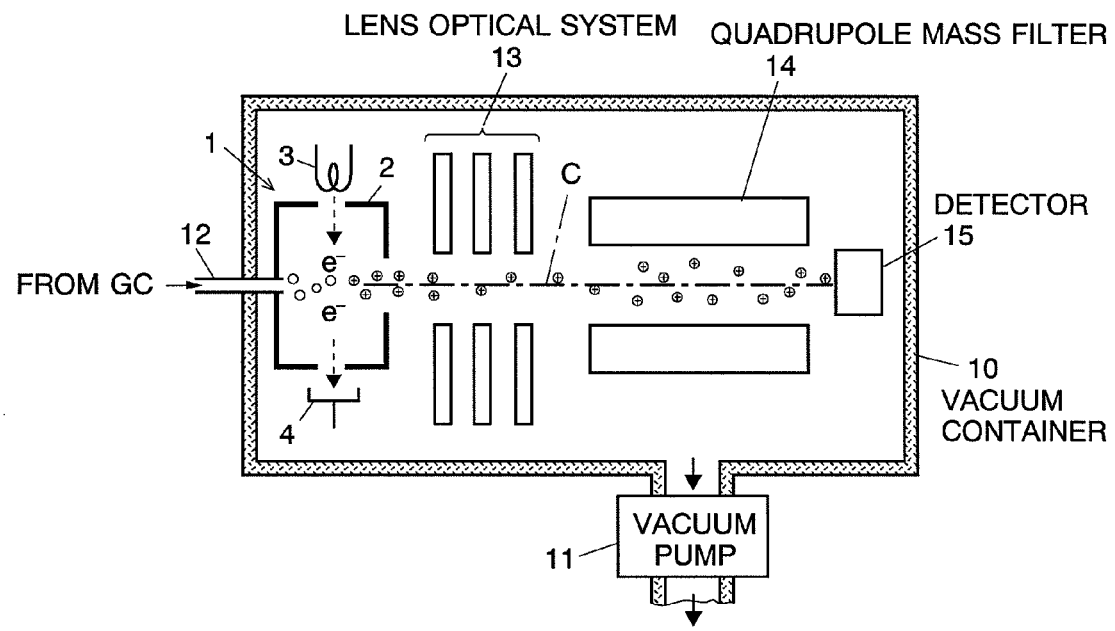
FIG. 1 is an overall configuration diagram of a mass spectrometer according to an embodiment of the present invention.

A mass spectrometer according to an embodiment of the present invention is hereinafter described with reference to the attached drawings. FIG. 1 is an overall configuration diagram of a mass spectrometer according to the present embodiment, and FIG. 2 is a detailed configuration diagram of an ion source.

In FIG. 1, the vacuum container 10 is a substantially hermetically sealed container, which is evacuated by a vacuum pump 11. Contained in this container are an ion source 1, a lens optical system 13, a quadrupole mass filter 14 and an ion detector 15, all being arranged along an ion optical axis C. A sample, such as a sample gas coming from the column of a gas chromatograph (not shown), is supplied through an appropriate interface and the introduction pipe 12 into the ion source 1. The sample molecules contained in the sample gas are ionized in this ion source 1.

Various kinds of ions thus produced are extracted rightward from the ion source 1, then converged by the lens optical system 13 and introduced into the space extending along the longitudinal axis of the quadrupole mass filter 14 consisting of four rod electrodes. A voltage consisting of a radio-frequency voltage superposed on a DC voltage is applied from a power source (not shown) to the quadrupole mass filter 14, and only the ions having a mass-to-charge ratio corresponding to the applied voltage can pass through the axially-extending space and arrive at, and detected by, the ion detector 15. The other, unnecessary ions cannot pass through the axially-extending space of the quadrupole mass filter 14; they will be diverged and lost halfway. Accordingly, it is possible, for example, to perform a scan operation in which the voltage applied to the quadrupole mass filter 14 is scanned over a predetermined range so that the mass-to-charge ratio at which the ions can reach the ion detector 15 will change over a predetermined mass range, and to create a mass spectrum from the detection signals obtained by this operation.

Figure 2:
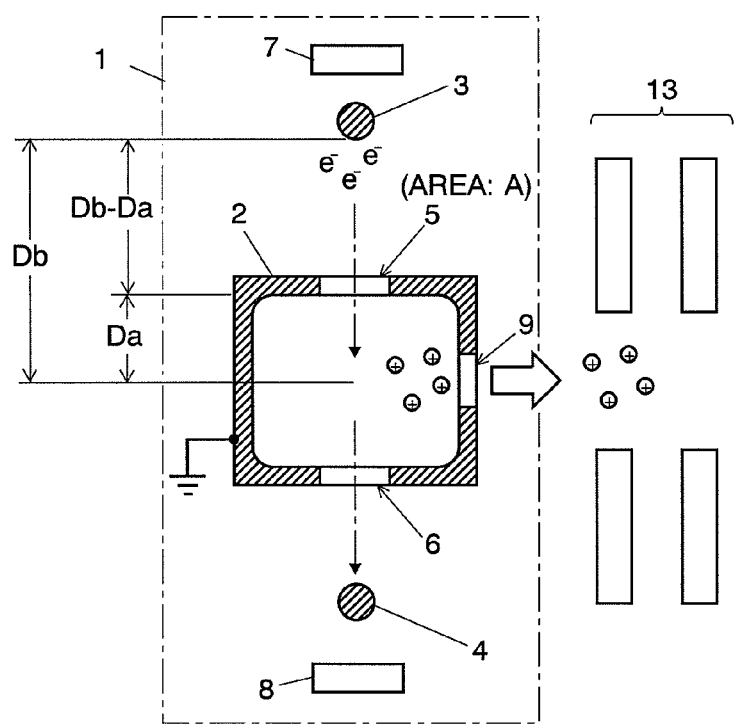
FIG. 2 is a configuration diagram of the ion source in the mass spectrometer according to the embodiment.

With reference to FIG. 2 in addition to FIG. 1, the structure of the ion source 1 performing electron ionization is hereinafter detailed. The ionization chamber 2 has a substantially box-shaped body made of a metal such as stainless steel, to which the sample introduction pipe 12 is connected. A sample gas containing sample molecules is supplied through this pipe 12 into the ionization chamber 2. This chamber 2 has an ion ejection port 9 on the ion optical axis C, and ions can be extracted through this port 9 to the outside. The ionization chamber 2 also has an electron injection port 5 and electron ejection port 6 that are respectively formed in the two walls facing each other across the ion optical axis C. A filament 3 is provided outside the electron injection port 5, and another filament that is identical in shape to the filament 3 is provided as the trap electrode 4 outside the electron ejection port 6.

When a heating current is supplied from a heating current source (not shown) to the filament 3, the temperature of the filament 3 rises and thermions are emitted from it. Due to the action of an electric field to be described later, the emitted thermions are accelerated toward the trap electrode 4 and pass through the ionization chamber 2 along the thermionic current axis L, which is substantially perpendicular to the ion optical axis C. The reason for the use of the trap electrode 4 being identical in shape to the filament 3 is to enable the two filaments to exchange their functions. In addition, a pair of magnets 7 and 8 are provided outside the filament 3 and the trap electrode 4, respectively. These magnets 7 and 8 create a magnetic field within the space between the filament 3 and the trap electrode 4.

The critical factors for the mass spectrometer of the present embodiment are the position of the filament 3 relative to the ionization chamber 2 and the relationship between this position and the opening area of the electron injection port 5. The first factor is that the ratio of Da, which is the distance between the center S of the ionization chamber 2 and the inner surface of the wall of the ionization chamber 2 in which the electron injection port 5 is formed, to Db, which is the distance between the center S and the filament 3, is set at 1.7 or larger in the present embodiment, whereas this ratio Db/Da was generally set at 1.5 or smaller in conventional mass spectrometers. This means that the filament 3 in the present embodiment is farther from the electron injection port 5 than in the conventional cases. The second factor is that the ratio A/(Db-Da) is determined within a range from 0.45 to 4.037, where A is the opening area of the electron injection port 5, and Db-Da is the distance between the inner surface of the ionization chamber 2 and the filament 3. The reason for this limitation will be explained later.

For example, the present system has the following voltage settings: the ionization chamber 2 is grounded (voltage=0 [V]), the filament 3 is −70[V], and the trap electrode 4 is 0[V]. This setting creates an electron-accelerating electric field in the space between the filament 3 and the ionization chamber 2 with a potential gradient that acts on an electron to accelerate it from the filament 3 to the ionization chamber 2. Meanwhile, a predetermined voltage whose polarity opposes that of the ions is applied to the lens electrodes 13. The potential difference between the lens optical system 13 and the ionization chamber 2 creates an electric field, a portion of which penetrates through the ion ejection port 9 into the ionization chamber 2 and acts on the ions to extract them through the ion-ejection port 9 to the outside.

The thermions generated by the filament 3 are accelerated by the aforementioned thermion-accelerating electric field and enters the ionization chamber 2 through the electron injection port 5. When a thermion (e⁻) comes in contact with a sample molecule (M), a molecule ion M⁺˙ is produced by the following reaction: $M+e^-\rightarrow M^{+\cdot}+2e^-$. The resultant thermions eventually exit from the electron ejection port 6 to the outside of the ionization chamber 2 and arrive at the trap electrode 4, thus producing a trap current in the trap electrode 4. The positive ion generated in the ionization chamber 2 is extracted from the ionization chamber 2 through the ion ejection port 9 by the aforementioned ion-extracting electric field.

The number of electrons captured by the trap electrode 4 depends on the number of electrons emitted from the filament 3. Accordingly, a control circuit (not shown) is provided to control the heating current supplied to the filament 3 so that the trap current produced by the electrons arriving at the trap electrode 4 is maintained at a predetermined level. This operation makes the filament 3 generate thermions at an approximately constant rate, and thereby stabilizes the production of ions within the ionization chamber 2. In the ionization process, the thermions do not directly fly to the trap electrode 4, but each thermion follows a spiral path due to the action of the magnetic field created by the magnets 7 and 8. The spiral path enables the thermion to stay longer in the ionization chamber 2 and accordingly have a greater chance of coming in contact with sample molecules, whereby the ionization efficiency is improved.

As in the conventional cases, if the filament 3 was in the vicinity of the electron injection port 5, the thermion-accelerating electric field created by the potential difference between the filament 3 and the ionization chamber 2 would penetrate through the electron injection port 5 into the ionization chamber 2 and thereby disturb the ion-extracting electric field within the ionization chamber 2, causing a portion of the ions to easily diverge from the path to the ion ejection port 9 and exit from the electron injection port 5 to the outside or collide with the inner surface of the ionization chamber 2. On the other hand, in the mass spectrometer according to the present invention, the filament 3 is located at a remote place so that the inner space of the ionization chamber 2 is free from the influence of the thermion-accelerating electric field created by the filament 3. Furthermore, the relationship between the opening area of the electron injection port 5 and its distance from the filament 3 is limited since the degree of penetration of the thermion-accelerating electric field into the ionization chamber 2 also depends on the opening area. As a result, the influence of the thermion-accelerating electric field within the ionization chamber 2 is almost completely eliminated and the ion-extracting electric field is free from disturbance, whereby the ion extraction efficiency is improved.

The inventors have conducted an experiment for determining the relationship between the value of Db/Da and the signal strength of the ion detector 15 under the condition that the opening area A of the electron injection port 5 and the distance (Db-Da) between the filament 3 and the inner surface of the wall the ionization chamber 2 satisfy the previously specified condition. The result demonstrated that, with a value of 1 representing the signal strength observed when Db/Da=1.4, the signal strength increased with an increase in Db/Da, and was nearly saturated at around 1.4 when Db/Da was 1.7 or larger. This result shows that it is possible to improve the ion extraction efficiency and achieve a signal strength higher than the conventional levels on an overall basis by setting Db/Da at 1.7 or larger.

Increasing the distance of the filament 3 from the electron injection port 5 naturally makes it more difficult for thermions to enter the ionization chamber 2, and consequently decreases the electron density of the thermionic current, so that the ion production efficiency most likely decreases. However, this decrease in the ion production efficiency can be cancelled by improving the ion production efficiency obtained by increasing the distance of the filament 3 from the electron injection port 5, so that a more favorable situation can be achieved for improving the detection sensitivity.

It is obvious that the preceding embodiment is a mere example, and any changes, modifications or additions can be made within the spirit and scope of the present invention.

The invention claimed is:

1. A mass spectrometer having an ion source that performs electron ionization, the ion source having a filament for generating thermions by heating and an ionization chamber in which sample molecules are ionized by the thermions, the ionization chamber having an electron injection port through which the thermions are introduced into an inner space thereof, wherein:
   a ratio Db/Da is 1.7 or larger, where Da is a distance between an inner surface of a wall of the ionization chamber in which the electron injection port is formed and a center of the ionization chamber, and Db is a distance between the filament and the center of the ionization chamber, the ratio indicating that the filament is located at a place so remote from the ionization chamber that the inner space of the ionization chamber is free from an influence of an electric field created in a space between the filament and the electron injection port by a potential difference between the filament and the ionization chamber.

2. The mass spectrometer according to claim 1, wherein a ratio A/(Db-Da) is within a range from 0.45 to 4.037 under a condition that the potential difference between the filament and the ionization chamber is within a range from 10 to 200[V], where A is an opening area (in units of mm²) of the electron injection port and Db-Da is a distance (in units of mm) between the filament and the inner surface of the wall of the ionization chamber in which the electron injection port is formed.

3. The mass spectrometer according to claim 1, wherein the ratio Db/Da is 3.0 or smaller.

4. The mass spectrometer according to claim 1, wherein:
   an electron ejection port is formed in a wall of the ionization chamber that is opposite to another wall of the ionization chamber in which the electron ejection port is formed;
   another filament that is identical in shape to the aforementioned filament is provided as a trap electrode outside the electron ejection port; and
   a positional relationship between the trap electrode and the ionization chamber is identical to a positional relationship between the aforementioned filament and the ionization chamber so as to enable the two filaments to exchange their functions.

* * * * *